(12) United States Patent
Anderson et al.

(10) Patent No.: US 10,207,810 B2
(45) Date of Patent: Feb. 19, 2019

(54) OPTICALLY DETECTING CLOUD METRICS USING SAMPLED ANALOG MEASUREMENTS OF LIGHT REFLECTION

(71) Applicant: Rosemount Aerospace Inc., Burnsville, MN (US)

(72) Inventors: Kaare Josef Anderson, Farmington, MN (US); Mark Ray, Burnsville, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 49 days.

(21) Appl. No.: 15/075,735

(22) Filed: Mar. 21, 2016

(65) Prior Publication Data

US 2017/0268993 A1 Sep. 21, 2017

(51) Int. Cl.
*B64D 15/20* (2006.01)
*G01N 15/02* (2006.01)
(Continued)

(52) U.S. Cl.
CPC ......... *B64D 15/20* (2013.01); *G01N 15/0205* (2013.01); *G01N 15/1434* (2013.01);
(Continued)

(58) Field of Classification Search
CPC ...... G01N 21/21; G01N 21/211; G01N 21/47; G01N 21/4738; G01N 21/4795;
(Continued)

(56) References Cited

U.S. PATENT DOCUMENTS 3,519,354 A * 7/1970 Hazel ............... G01N 21/538
250/574
3,782,824 A * 1/1974 Stoliar ............. G01N 21/538
356/342

(Continued)

FOREIGN PATENT DOCUMENTS

JP 02189444 A * 7/1990

OTHER PUBLICATIONS

Halama, Gary E. et al., "Optical Ice Detection: Test Results from the NASA Glenn Icing Research Tunnel," 2010, American Institute of Aeronautics aand Astronautics, Inc., pp. 1-13.*

(Continued)

*Primary Examiner* — Gordon J Stock, Jr.
(74) *Attorney, Agent, or Firm* — Kinney & Lange, P.A.

(57) ABSTRACT

Apparatus and associated methods relate to determining metrics of water particles in clouds by directing light pulses at a cloud and measuring a peak, a post-peak value and a high-frequency fluctuation of light signals reflected from the cloud. The light pulses include: a first pulse having circularly polarized light of a first wavelength; and a second pulse of a second wavelength. The reflected light signals include: a first reflected light signal having left-hand circular polarization of the first wavelength; a second reflected light signal having right-hand circular polarization of the first wavelength; and a third reflected light signal of the second wavelength. An extinction coefficient and a backscatter coefficient are determined based on the measured peak and post-peak slopes of the first and second reflected light signals. The measured high-frequency fluctuations of the three reflected light signals can be used to calculate cloud particle sizes.

16 Claims, 4 Drawing Sheets

(51) Int. Cl.
*G01W 1/00* (2006.01)
*G01N 21/53* (2006.01)
*G01S 7/48* (2006.01)
*G01S 7/481* (2006.01)
*G01S 7/499* (2006.01)
*G01S 7/486* (2006.01)
*G01S 17/95* (2006.01)
*G01N 21/21* (2006.01)
*G01N 15/14* (2006.01)
*G01N 21/47* (2006.01)
*B64D 47/04* (2006.01)
*G01N 21/17* (2006.01)

(52) U.S. Cl.
CPC ........... *G01N 21/21* (2013.01); *G01N 21/538* (2013.01); *G01S 7/4802* (2013.01); *G01S 7/4815* (2013.01); *G01S 7/4865* (2013.01); *G01S 7/499* (2013.01); *G01S 17/95* (2013.01); *G01W 1/00* (2013.01); *B64D 47/04* (2013.01); *G01N 2021/1795* (2013.01); *G01N 2021/216* (2013.01); *G01N 2021/4709* (2013.01); *G01N 2021/4792* (2013.01); *G01N 2201/0697* (2013.01); *Y02A 90/19* (2018.01)

(58) Field of Classification Search
CPC ...... G01N 21/49; G01N 21/53; G01N 21/538; G01N 21/55; G01N 2015/0023; G01N 2015/0026; G01N 2015/0042; G01N 2015/0046; G01N 15/02; G01N 15/0205; G01N 15/0211; G01N 15/06; G01N 15/1434; G01N 2201/0697; G01N 2201/06113; G01N 2201/12; G01N 2021/1793; G01N 2021/1795; G01N 2021/216; G01N 2021/4792; G01N 2021/4709; G01S 7/4865; G01S 7/4803; G01S 7/4815; G01S 7/499; G01S 17/95; B64D 15/20; B64D 47/04; G01J 4/00; G01J 4/02; G01J 4/04; G01J 2004/001; G01J 2004/002; G01J 2004/004; G01J 2004/005; G01J 2004/007; G08B 19/02; G01W 1/00

USPC ................. 356/337, 342, 445, 446, 364–370
See application file for complete search history.

(56) References Cited

U.S. PATENT DOCUMENTS

| | | | | |
|---|---|---|---|---|
| 4,015,135 | A * | 3/1977 | Tipton, Jr. | ......... G01N 15/0227 250/564 |
| 5,173,750 | A * | 12/1992 | Laukaitis | ................. G01J 1/16 250/214 B |
| 5,596,320 | A | 1/1997 | Barnes | |
| 6,069,565 | A | 5/2000 | Stern et al. | |
| 6,384,903 | B1 * | 5/2002 | Fuller | ....................... G01J 3/42 356/301 |
| 6,825,471 | B1 * | 11/2004 | Shulga | ............... G01N 21/1702 250/343 |
| 6,914,674 | B1 * | 7/2005 | Wang | .................. G01N 21/532 250/573 |
| 7,986,408 | B2 * | 7/2011 | Ray | ........................ B64D 15/20 356/342 |
| 8,144,325 | B2 * | 3/2012 | Ray | ........................ B64D 15/20 356/342 |
| 8,338,785 | B2 | 12/2012 | Ray | |
| 8,831,884 | B2 | 9/2014 | Ray et al. | |
| 9,041,926 | B2 * | 5/2015 | Ray | ........................ G01S 17/95 356/342 |
| 9,116,243 | B1 * | 8/2015 | Brown | .................... G01S 17/95 |
| 2006/0262324 | A1 | 11/2006 | Hays et al. | |
| 2010/0110431 | A1 * | 5/2010 | Ray | ....................... B64D 15/20 356/342 |
| 2012/0274938 | A1 | 11/2012 | Ray | |
| 2013/0103317 | A1 | 4/2013 | Ray et al. | |
| 2013/0284856 | A1 | 10/2013 | Botura et al. | |
| 2014/0379263 | A1 | 12/2014 | Ray et al. | |

OTHER PUBLICATIONS

Extended European Search Report, for European Patent Application No. 17158328.9, dated Jul. 28, 2017, 10 pages.

* cited by examiner

OPTICALLY DETECTING CLOUD METRICS USING SAMPLED ANALOG MEASUREMENTS OF LIGHT REFLECTION

BACKGROUND

When an aircraft travels through clouds, there may be a potential for ice formation on the aircraft. If the ice forms on control surfaces and/or lift surfaces, the aircraft's flight may be jeopardized. Not every cloud, however, presents a dangerous risk of ice formation on an aircraft. Different clouds and different atmospheric conditions may be accompanied by various water droplet size distributions, different ice/liquid ratios, etc. Such water droplet size distributions and ice/liquid ratios may be measured as cloud metrics using various instruments.

Many aircraft are equipped with these instruments to detect and/or measure such cloud metrics. These detected and measured cloud metrics may be used to predict whether a particular cloud can have conditions conducive to ice formation on control or lift surfaces. Such cloud metrics may even be used to predict the location(s) on the aircraft where such ice formation could be expected. One such system for measuring cloud metrics is called an Optical Icing Conditions Detector (OICD). Some OICD systems may direct one or more pulsed lasers into a cloud formation. The OICD system may then measure a light signal reflected by the cloud formation.

Complex signal analyses of these reflected light signals may be performed to determine the various cloud metrics being measured. Such complex signal analyses may require powerful computers and extensive computations. Such powerful systems and extensive computations may result in voluminous and/or heavy system components, high power-consuming electronics, and/or expensive aircraft avionics.

SUMMARY

An Optical Icing Conditions Detector (OICD) includes a pulsed laser system configured to generate a first pulse of circularly polarized light having a first wavelength. The optical icing conditions detector includes two analog channels. Each of the two analog channels includes a peak detector configured to generate a signal indicative of a peak of a light signal reflected by a cloud. Each of the two analog channels includes a post-peak slope detector configured to generate a signal indicative of a rate of decay of the light signal reflected by the cloud. The rate of decay corresponds to a time following a time of the detected peak. A first of the two channels is configured to operate on a first reflected light signal corresponding to light of the first pulse reflected by the cloud. The first reflected light signal has a left-hand circular polarization. A second of the two channels is configured to operate on a second reflected light signal corresponding to light of the first pulse reflected by the cloud. The second reflected light signal has a right-hand circular polarization.

A method of determining an ice/liquid ratio in a cloud includes directing a first pulse of circularly polarized light having a first wavelength at a cloud. The method includes sampling and holding a peak and a post-peak slope of a first reflected light signal corresponding to light of the first pulse reflected by the cloud. The first reflected light signal has a left-hand circular polarization. The method includes sampling and holding a peak and a post-peak slope of a second reflected light signal corresponding to light of the first pulse reflected by the cloud. The second reflected light signal has a right-hand circular polarization. The method includes determining, for at least one of the first and second reflected light signals, an extinction coefficient. The method also includes determining, for each of the first and second reflected light signals, a backscatter coefficient.

DETAILED DESCRIPTION

Apparatus and associated methods relate to an optical icing conditions detector that uses a reduced number of signal values to determine cloud metrics. By using a reduced number of signal values, a low-speed analog-to-digital converter and/or a low-speed microprocessor can be used for calculating various cloud metrics. Instead of using a high-speed analog-to-digital converter for sampling of light signals reflected from clouds, only a limited number of samples of the reflected light signals are taken at specific times. The number of samples taken is greater than or equal to the number of model parameters to be calculated. The calculated model parameters then can be used to determine the various cloud metrics.

Figure 1:
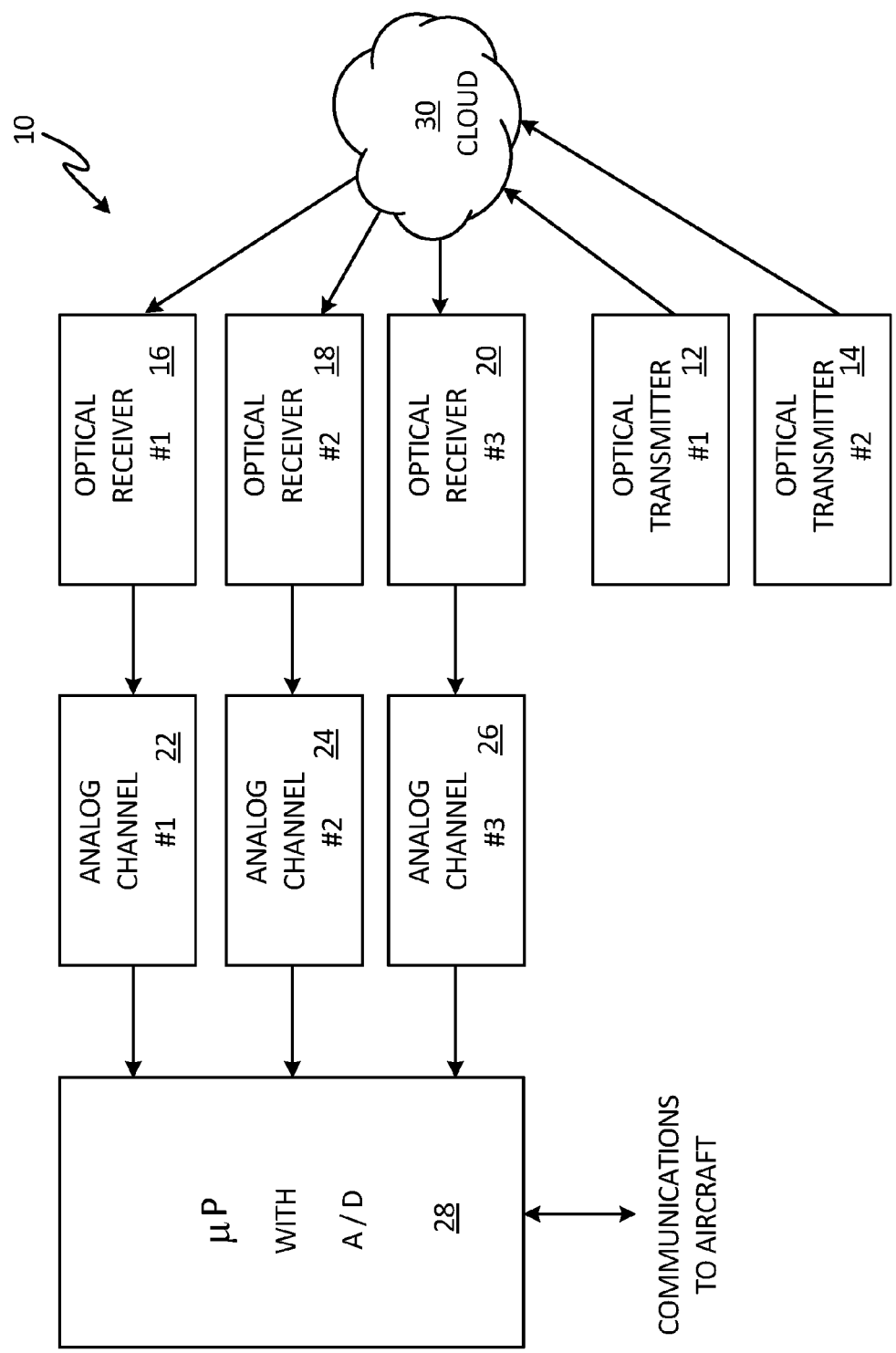
FIG. 1 is a schematic diagram of an exemplary optical icing conditions detection system using two-color illumination and three channel detection.

FIG. 1 is a schematic diagram of an exemplary optical icing conditions detection system using two-color (e.g., electromagnetic waves of two different wavelengths) illumination and three channel detection. In FIG. 1, optical icing conditions detection (OICD) system 10 includes: two optical transmitters 12, 14; three optical receivers 16, 18, 20; three analog channels 22, 24, 26, and a microprocessor and/or microcontroller 28. Each of the two optical transmitters 12, 14 are configured to direct a pulse of light energy into a cloud 30.

First optical transmitter 12, for example, can be configured to direct a first laser pulse having a first wavelength and having a first polarization into the cloud 30. Second optical transmitter 14 can be configured to direct a second laser pulse having a second wavelength into the cloud 30. In some embodiments, a first polarization may be a linear polarization. In some embodiments a first polarization may be a circular polarization, such as, for example a right-hand circular polarization or a left-hand circular polarization. In some combinations the first polarization can be a combination of these polarizations.

Each of the three optical receivers 16, 18, 20 is configured to receive light directed into cloud 30 by one of optical transmitters 12, 14 and reflected by cloud 30. A polarization of the light reflected by cloud 30 can change as a result of interaction with water droplets and/or ice crystals that makeup cloud 30. Each of optical receivers 16, 18, 20 can be tuned to detect light of a specific wavelength and of a specific polarization. The wavelength/polarization tuning of each of the three optical receivers 16, 18, 20 can be unique to it and can be different from one another.

First optical receiver 16, for example, can be configured to receive a first reflected light signal corresponding to light directed into cloud 30 by first optical transmitter 12 and reflected from cloud 30. The first reflected light signal can have the first wavelength and the first polarity. In some embodiments the first wavelength can correspond to light having a relatively low water absorption coefficient. For example, various embodiments may have a first wavelength corresponding to light having a water absorption coefficient of less than 100 m$^{-1}$, less than 30 m$^{-1}$, or less than 10 m$^{-1}$. In an exemplary embodiment, the first wavelength may be about 905 nm.

Second optical receiver 18 can be configured to receive a second reflected light signal corresponding to light directed into cloud 30 by first optical transmitter 12 and reflected from cloud 30. The second reflected light signal can have the first wavelength and the polarity different from the first polarity.

Third optical receiver 20 can be configured to receive a third reflected light signal corresponding to light directed into cloud 30 by second optical transmitter 14 and reflected from cloud 30. In some embodiments, the third reflected light signal can have the second wavelength. In some embodiments the second wavelength can correspond to light having a relatively high water absorption coefficient. For example, various embodiments may have a first wavelength corresponding to light having a water absorption coefficient of greater than 300 m$^{-1}$, greater than 1000 m$^{-1}$, or greater than 3000 m$^{-1}$. In an exemplary embodiment, the second wavelength may be about 1550 nm.

Each of the three analog channels 22, 24, 26 corresponds to a different one of the three optical receivers 16, 18, 20, respectively. Analog channels 22, 24, 26 can perform analog signal processing to each of the signal pulses received by optical receivers 16, 18, 20. Each of the three analog channels 22, 24, 26 can perform analog signal processing and can sample and hold a limited number of analog signals. For example, each of analog channels 22, 24, 26 can have a peak detector, one or more sample and hold circuits and a high-frequency signal power detector. In some embodiments, each of the analog channels 22, 24, 26 can provide five or fewer analog signals per received pulse for subsequent processing by microprocessor 28.

Microprocessor 28 can have a low-speed analog-to-digital converter for converting the analog signals provided by the analog channels 22, 24, 26. Processing all of the analog signals provided by all three analog channels 22, 24, 26 can require as few as fifteen analog-to-digital conversions, for example. Because so few analog signals are provided to microprocessor 28, and because analog channel 22, 24, 25 can perform some of the signal processing necessary to calculate could metrics, microprocessor 28 can be a low cost component and/or a low power component.

As illustrated in FIG. 1, optical icing conditions detection system 10 can include microprocessor 10, respectively. Microprocessor 10, in one example, is configured to implement functionality and/or process instructions for execution within optical icing conditions detection system 10, respectively. For instance, microprocessor 10 can be capable of processing instructions stored in program memory. Examples of microprocessor 10 can include any one or more of a microprocessor, a controller, a digital signal processor (DSP), an application specific integrated circuit (ASIC), a field-programmable gate array (FPGA), or other equivalent discrete or integrated logic circuitry.

Figure 2:
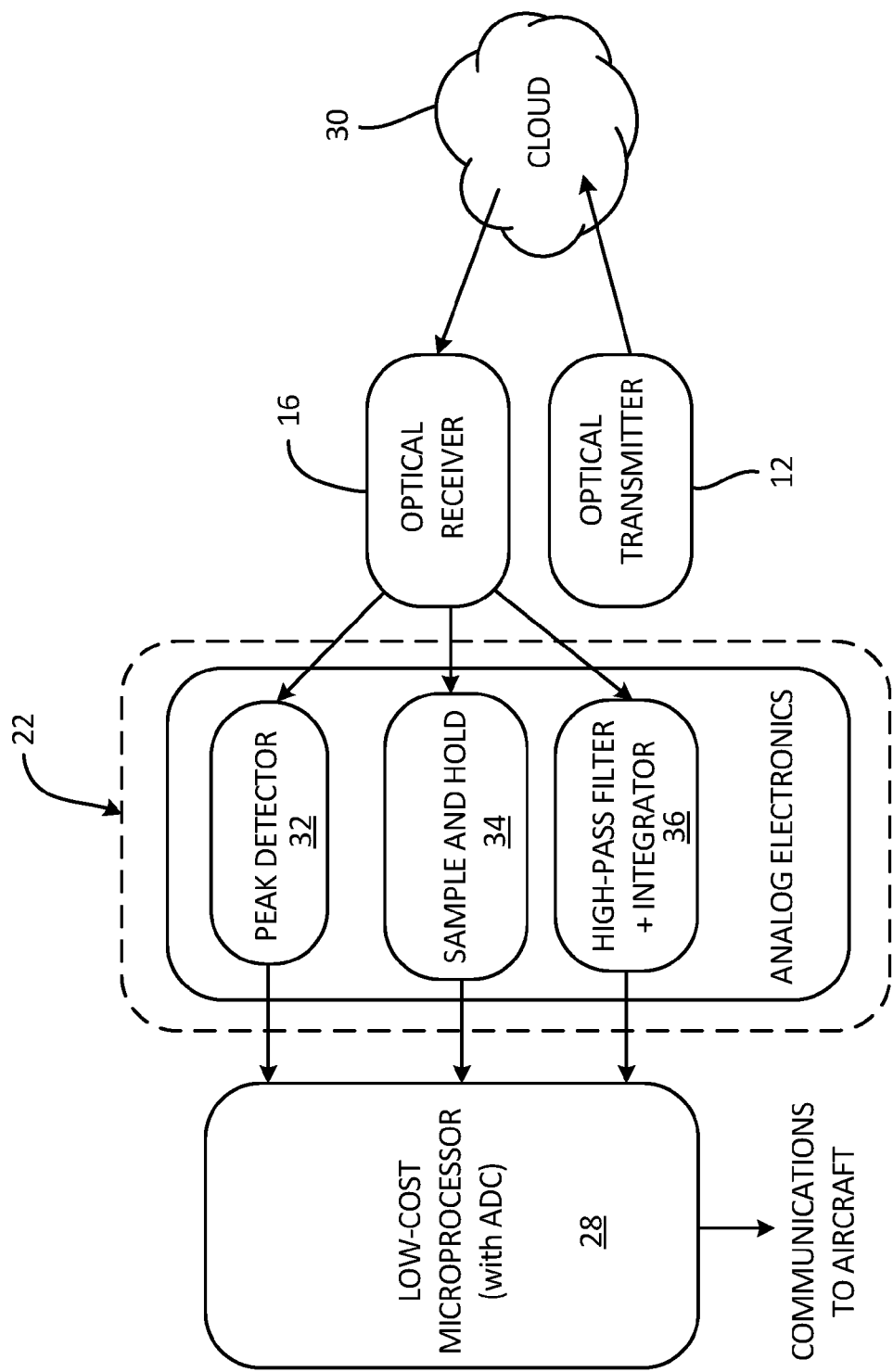
FIG. 2 is a schematic view of a single detection channel of an exemplary optical icing conditions detection system.

FIG. 2 is a schematic view of a single detection channel of an exemplary optical icing conditions detection system. FIG. 2 depicts a single analog channel (e.g., analog channel 22) corresponding to a single optical receiver (e.g., Optical receiver 16) of OICD system 10 depicted in FIG. 1. Optical receiver 16 generates an electrical output signal in response to receiving a light signal reflected from cloud 30. Optical receiver 16 then outputs the generated electrical output signal to analog channel 22. Analog channel 22 includes peak detector 32, Sample and hold component 34 and high-pass filter and integrator 36.

Peak detector 32 can detect a peak of the received electrical output signal. Peak detector 32 can generate and provide a signal indicative of the detected peak. In some embodiments, peak detector 32 can also generate and provide a signal indicative of a time corresponding to the detected peak.

Sample and hold component 34 can sample and hold the electrical output signal at one or more specific times subsequent to the time corresponding to the detected peak or to a laser pulse emitted from an optical transmitter. For example, sample and hold component 34 can sample and hold the electrical output signal at two distinct times following the time of the detected peak or the laser pulse. In some embodiments, sample and hold component 34 can sample and hold the electrical output signal at only one time following the time of the detected peak. In an exemplary embodiment, sample and hold component 34 can generate a signal corresponding to a time derivative of the electrical output signal. Sample and hold component 34 can then act as a peak detector and detect a peak in the time derivative of the electrical output signal. In some embodiments, sample and hold component 34 measures a time interval between when the signal drops below two different threshold values. Sample and hold component 34 then provides electrical signals corresponding to the electrical signals sampled and held to microprocessor 28 and/or an analog-to-digital converter for further processing.

High-pass filter and integrator 36 also operates on the electrical output signal provided by optical receiver 16. High-pass filter and integrator 36 generates a signal indicative of a high-frequency fluctuation of the electrical output signal. Various methods of measuring the high-frequency fluctuation of the electrical output signal can be employed. For example, the electrical output signal can be high-pass filtered and the power of the resulting signal can be measured. Various methods can be used to measure the power of a signal. For example, the high-pass filtered signal can be squared (e. g., multiplied by itself) and then the resulting signal can be integrated over a predetermined time period. In an exemplary embodiment, a peak detector can simply detect the peak of the high-pass filtered signal. This detected peak can be indicative of a magnitude of the high-frequency fluctuation of the electrical output signal.

Various embodiments may measure reflection fluctuations in various manners. In some embodiments, reflection fluctuations can be detected without using a high-pass filter. In an exemplary embodiment, for example, a reflection fluctuation detector can detect variations between detected peaks in a sequence of reflected pulses that can be used as a metric indicative of high-frequency fluctuations. In some embodiments, variations in the detected peaks of a series of reflected light signals, variations in detected sample and hold signals from a series of reflected light signals or a combination of both can be used to determine high-frequency fluctuations of the electrical output signal in a channel. In such embodiments, even fewer sampled signals per reflected light signal pulse would require analog-to-digital conversion. In an exemplary embodiment, a detected peak and a detected peak slope can be sufficient to determine both a backscatter coefficient and an optical extinction coefficient. The backscatter coefficient and the optical extinction coefficient will be described below.

Figure 3:
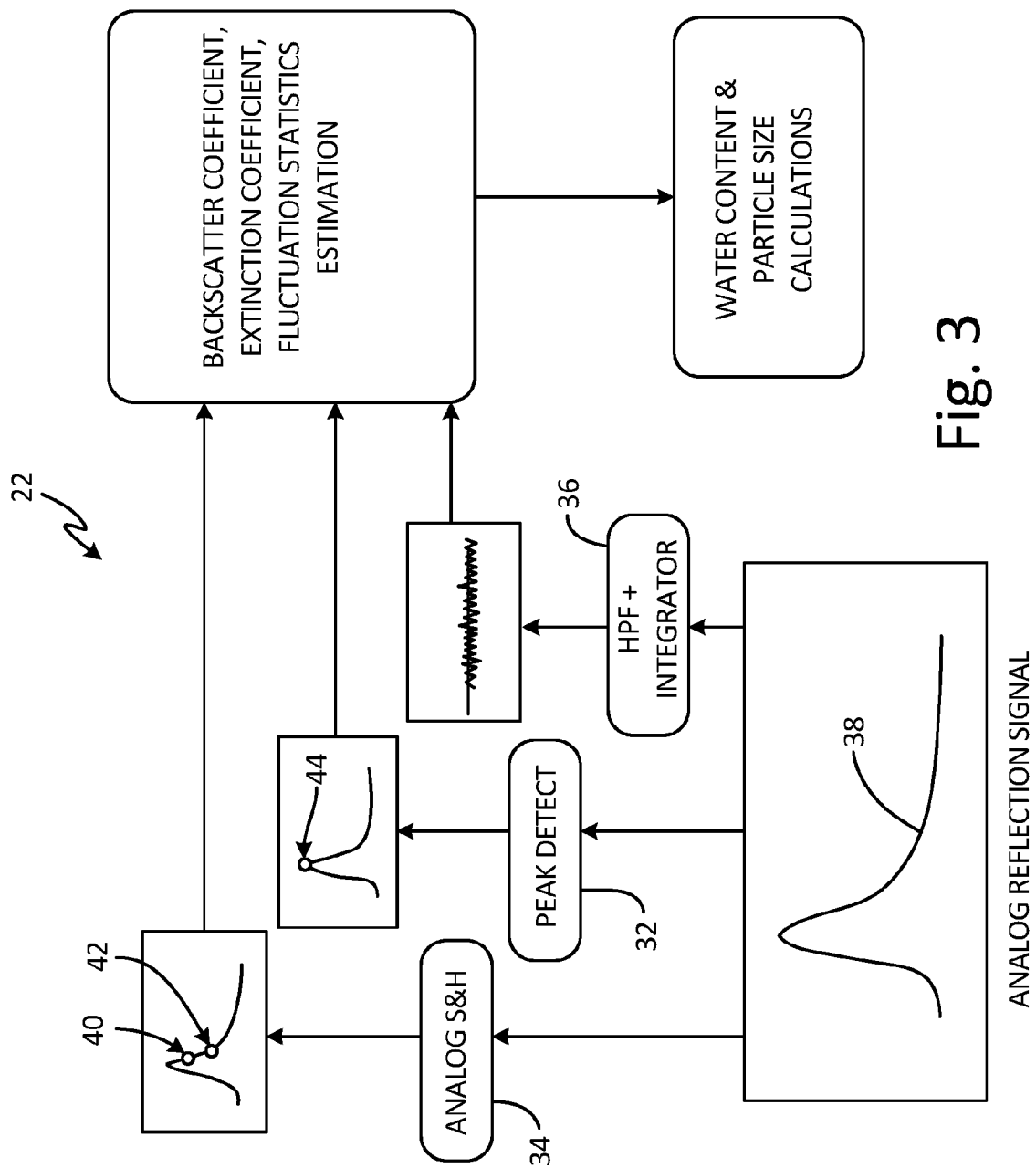
FIG. 3 is a schematic view of exemplary analog channel, in which signal processing waveforms are depicted

FIG. 3 is a schematic view of exemplary analog channel, in which signal processing waveforms are depicted. In FIG. 3, exemplary analog channel 22 is depicted along with exemplary waveforms and exemplary analog measurements. Analog channel 22 receives analog reflection signal 38 from optical receiver 16 (depicted in FIG. 1). Analog reflection signal 38 is then provided to each of peak detector 32, analog sample and hold component 34, and signal high-frequency detector 36.

Peak detector 32 detects and generates a signal indicative of peak 44 of analog reflection signal 38. Analog sample and hold component 34 generates two sampled signals 40, 42 of analog reflection signal 38. Each of the two sampled signals 40, 42 corresponds to a time that is subsequent to a time of the detected peak. High-frequency detector 36 generates a signal indicative of a magnitude of high-frequency fluctuations 46 superimposed on reflection signal 38. Each analog reflection signal 38 can be fit to a model equation, such as equation (3) of paragraph [0026] disclosed by Ray et al. in U.S. published application 2013/0103317, filed Oct. 25, 2011, titled "Methods of Determining the Liquid Water Content of a Cloud," the entire disclosure (henceforth referred to as "the '317 publication") of which is hereby incorporated by reference. Peak 44, and one or more sample and hold signals 40, 42 can be used to calculate a backscatter coefficient and an optical extinction coefficient.

In the '317 publication, the model equation is given by:

$$N(R) = \beta e^{-2\alpha R} \quad (1)$$

Here, $N(R)$ is the normalized corrected echo intensities as a function of range R. Range R can be correlated to time in the analog reflection signal 38, as increasing time of reflection is indicative of a reflection from an increasing range. In equation (1), $\beta$ is the backscatter coefficient, and $\alpha$ is the optical extinction coefficient. Because both the backscatter coefficient $\beta$ and the optical extinction coefficient $\alpha$ are unknown coefficients to be fit to analog reflection signal 38, at least two analog signal values must be supplied by analog channel 22. For example, a peak and a single sample and hold signal is sufficient to obtain both the backscatter coefficient $\beta$ and the optical extinction coefficient $\alpha$. Or two sample and hold signals is sufficient to calculate both the backscatter coefficient $\beta$ and the optical extinction coefficient $\alpha$.

The '317 publication also discloses how the model can be used to calculate various cloud metrics, such as liquid water content (LWC), droplet size distributions, and ice/liquid water ratios. For example, use of both left-hand circularly polarized reflection signals and right-hand circularly polarized reflection signals can be used to calculate an ice/liquid water ratio. Furthermore, the high-frequency fluctuation of an analog reflection signal can be used to detect large droplets in a cloud formation, as disclosed by Ray et al. in U.S. published application 2014/0379263, filed Jun. 21, 2013, titled "Large Droplet Detection by Statistical Fluctuations in LIDAR Backscatter," the entire disclosure (henceforth referred to as "the '263 publication") of which is hereby incorporated by reference.

Paragraph [0024] of the '263 publication discloses that both spatial fluctuations (i.e. along the length of the cloud sampled by a single pulse from the OICD), and temporal fluctuations (i.e. from one laser pulse to the next) can be used to calculate a metric indicative of high-frequency fluctuations. High-frequency fluctuations can be indicative of large particles in the reflecting cloud. Particles having an average diameter larger than certain values can be problematic for an aircraft. For example particles having an average diameter larger than 40 microns, 100 microns, or 200 microns can present problems for an aircraft engine.

Temporal fluctuations can be measured by comparing sample and hold signals taken at substantially the same relative times from a series of analog reflection pulses 38. For example, peak 44 of analog reflection signal can be taken as a reference time, and substantially the same relative times for each of a series of reflected light signals can be measured with respect to each peak 44. In some embodiments, a reference time can be the specific time at which Optical transmitter 12 generates a laser pulse and directs the laser pulse to cloud 30. Relative times for each of a series of reflected light signals then can be measured with respect to the reference times determined by the generation and direction of the laser pulses.

An ice/liquid ratio of the water droplets in a cloud can be determined, as disclosed by Ray et al. in U.S. Pat. No. 7,986,408, filed Nov. 5, 2008, titled "Apparatus and Method for In-Flight Detection of Airborne Water Droplets and Ice Crystals," the entire disclosure (henceforth referred to as "the '408 patent") of which is hereby incorporated by reference. The 1 408 patent discloses: "Water droplets ideally act like perfect mirrors and scatter the reflected laser light back on itself without altering the polarization state. If the incident light is horizontally or vertically polarized, the reflected light is likewise horizontally or vertically polarized. Therefore, a backscatter polarization with a relatively low degree of depolarization is indicative of a liquid water cloud. In the case of circular polarization, the direction of the rotating electric field does not change upon reflection, but the change in Poynting vector of the incident wave changes the sense of circular polarization. Hence, an incident beam which is right hand circularly polarized becomes left hand circularly polarized upon reflection, and vice versa." (Col. 4, lines 4-24). Thus a ratio of reflected light of left-hand circular polarity to reflected light of right-hand circular polarity can be indicative of an ice/liquid ration of cloud water droplets.

Ice crystals, on the other hand, tend to alter the polarization state of reflected light, due in part to multiple internal reflections from their facets and in part to the birefringence of ice. Reflected light from airborne ice crystals becomes a mixture of two orthogonal polarization states when the incident light is a pure polarization state. By monitoring both orthogonal polarization states of the backscattered light, it is possible to distinguish water droplets from ice crystals.

Figure 4:
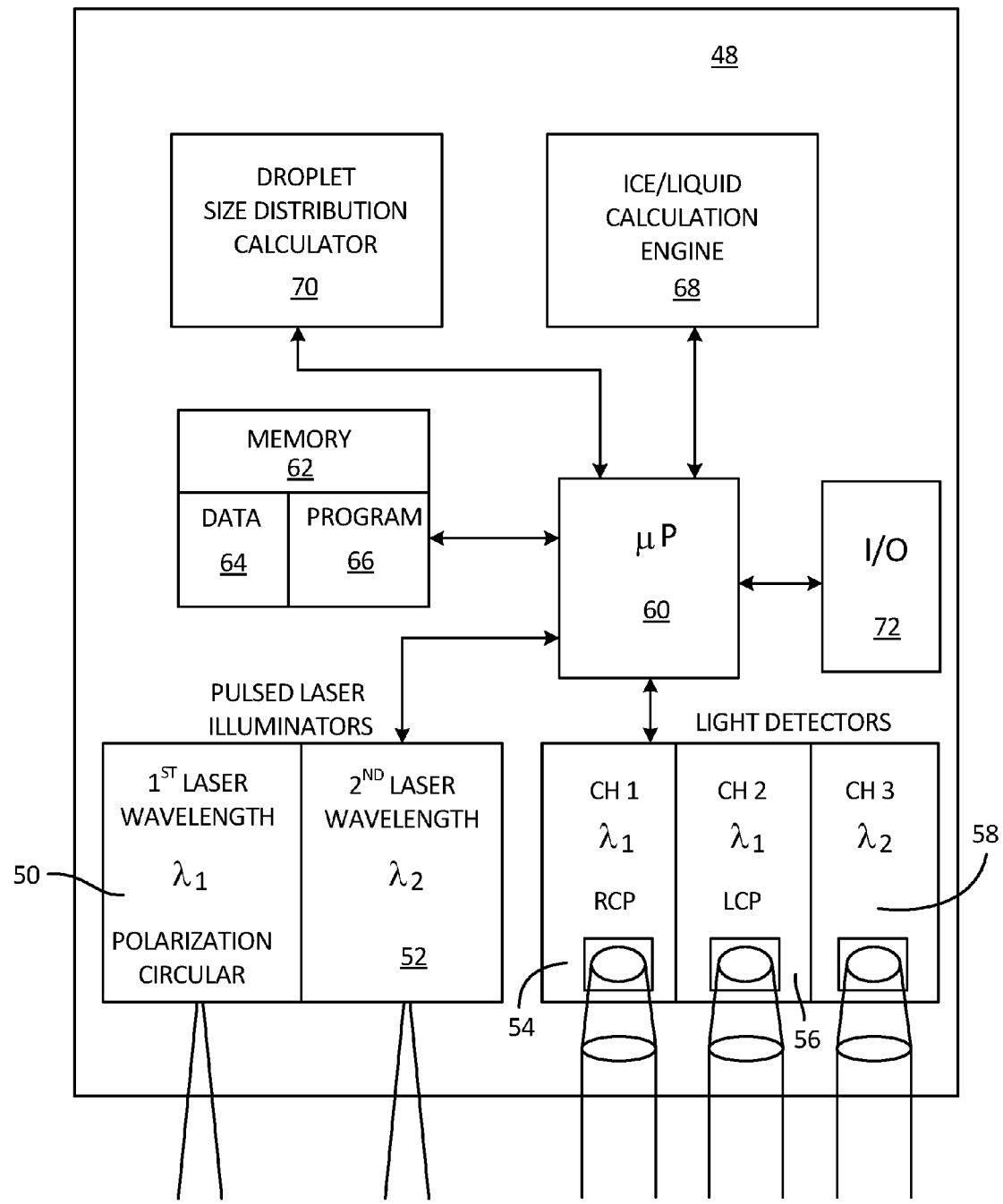
FIG. 4 is a block diagram of an exemplary optical icing conditions detector.

FIG. 4 is a block diagram of an exemplary optical icing conditions detector. In FIG. 4, optical icing conditions detector 48 includes: two pulsed laser illuminators 50, 52; three light detectors 54, 56, 58; microprocessor 60; memory 62 having data memory locations 64 and program memory locations 66; ice/liquid calculation engine 68; droplet size distribution calculator 70; and input/output interface 72. Each of the two pulsed laser illuminators 50, 52 generate a laser pulse of a specified wavelength and direct the generated pulse to a cloud. Each of the three light detectors 54, 56, 58 is then configured to receive light corresponding to one of the generated pulses and reflected from the cloud. Each of the three light detectors includes analog electronic systems to generate a limited number of analog signals to be converted to digital format by a digital processing system such as microprocessor 60.

Microprocessor 60 then receives the limited number of analog signals from the three light detectors 54, 56, 58 and converts the received analog signals to digital format. In some embodiments, the received analog signals include binary signals indicative of when the reflection of the optical signal falls below predetermined thresholds. Microprocessor 60 then calculates model parameters based on the received analog signals. Microprocessor communicates with data memory locations 64 and program memory locations 66 of memory 62. Microprocessor 60 communicates calculated model parameters to each of droplet size distribution calculator 70 and ice/liquid calculation engine 68. Droplet size distribution calculator 70 calculates, based on the calculated model parameters, a size distribution of water particles in the cloud. Droplet size distribution calculator 70 then communicates the calculated droplet size distribution to microprocessor 60. In some embodiments, droplet size distribution calculation is performed by microprocessor 60.

Ice/liquid calculation engine 68 calculates, based on the calculated model parameters, an ice/liquid ratio of water particles in the cloud formation. Ice/liquid calculation engine 68 then communicates the calculated ice/liquid ratio to microprocessor 60. In some embodiments, calculation of an ice/liquid ratio is performed by microprocessor 60. Microprocessor 60 in turn communicates both calculated droplet size distribution and ice/water ratio to a remote system via input/output interface 72. An exemplary remote system can be a cloud parameter indicator located in a cockpit of an aircraft.

The following are non-exclusive descriptions of possible embodiments of the present invention.

An optical icing conditions detector includes a pulsed laser system configured to generate a first pulse of circularly polarized light having a first wavelength. The optical icing conditions detector includes two analog channels. Each of the two analog channels includes a peak detector configured to generate a signal indicative of a peak of a light signal reflected by a cloud. Each of the two analog channels includes a post-peak slope detector configured to generate a signal indicative of a rate of decay of the light signal reflected by the cloud. The rate of decay corresponds to a time following a time of the detected peak. A first of the two channels is configured to operate on a first reflected light signal corresponding to light of the first pulse reflected by the cloud. The first reflected light signal has a left-hand circular polarization. A second of the two channels is configured to operate on a second reflected light signal corresponding to light of the first pulse reflected by the cloud. The second reflected light signal has a right-hand circular polarization.

A further embodiment of the foregoing optical icing conditions detector, wherein the pulsed laser system is further configured to generate a second pulse of light having a second wavelength. Any of the foregoing optical icing conditions detectors can optionally include, additionally and/or alternatively, any one or more of the following features, configurations and/or additional components: i) a third analog channel; ii) a microprocessor; and/or iii) an analog-to-digital converter. The third analog channel can include a peak detector configured to generate a signal indicative of a peak of a light signal reflected by a cloud. The third analog channel can a post-peak slope detector configured to generate a signal indicative of a rate of decay of the light signal reflected by the cloud. The rate of decay can follow the time of the peak.

A further embodiment of any of the foregoing optical icing conditions detectors, wherein each of the two analog channels can further include a reflection fluctuation detector configured to measure a magnitude of high-frequency fluctuation of the light signal reflected by the cloud. A further embodiment of any of the foregoing optical icing conditions detectors, wherein the microprocessor can be configured to calculate, based on the signal indicative of the rate of decay, an optical extinction coefficient. A further embodiment of any of the foregoing optical icing conditions detectors, wherein the microprocessor can be configured to calculate, based on the signal indicative of the peak and the signal indicative of the rate of decay, a backscatter coefficient. A further embodiment of any of the foregoing optical icing conditions detectors, wherein the microprocessor can be configured to calculate, based on a ratio of calculations based on signals from the first channel to calculations based on signals from the second channel, an ice/liquid ratio of the cloud. A further embodiment of any of the foregoing optical icing conditions detectors, wherein the microprocessor can be configured to calculate, based on the magnitude of high-frequency of fluctuation, a measure of a density of large particles in the cloud. A further embodiment of any of the foregoing optical icing conditions detectors, wherein the first wavelength can correspond to light having a water absorption coefficient less than 50 $m^{-1}$. A further embodiment of any of the foregoing optical icing conditions detectors, wherein the second wavelength is 1550 can correspond to light having a water absorption coefficient greater than 1000 $m^{-1}$. A further embodiment of any of the foregoing optical icing conditions detectors, wherein the post-peak slope detector can include two sample and hold circuits each configured to sample and hold a value of the light signal reflected by the cloud at different times subsequent to the time of the peak. A further embodiment of any of the foregoing optical icing conditions detectors, wherein the post-peak slope detector includes a differentiator configured to generate a signal indicative of a time derivative of the light signal reflected by the cloud. A further embodiment of any of the foregoing optical icing conditions detectors, wherein the post-peak slope detector includes a peak detector configured to generate a signal indicative of a peak of the signal indicative of the time derivative of the light signal reflected by the cloud.

A method of determining an ice/liquid ratio in a cloud includes directing a first pulse of circularly polarized light having a first wavelength at a cloud. The method includes sampling and holding a peak and a post-peak slope of a first reflected light signal corresponding to light of the first pulse reflected by the cloud. The first reflected light signal has a left-hand circular polarization. The method includes sampling and holding a peak and a post-peak slope of a second reflected light signal corresponding to light of the first pulse reflected by the cloud. The second reflected light signal has a right-hand circular polarization. The method includes determining, for at least one of the first and second reflected light signals, an extinction coefficient. The method also includes determining, for each of the first and second reflected light signals, a backscatter coefficient.

The method of the preceding paragraph can optionally include, additionally and/or alternatively, any one or more of the following features, configurations and/or additional components: i) directing a second pulse of light having a second wavelength at the cloud; ii) sampling and holding a peak and a post-peak slope of a third reflected light signal corresponding to light of the second pulse reflected by the cloud; iii) measuring a magnitude of high-frequency fluctuation of at least one of the first and second reflected light signals; iv) calculating, based on the extinction coefficient, a density of particles; v) calculating, based on the measured magnitude of high-frequency fluctuation, a density of large particles in a sparse cloud, wherein large particles have an average diameter greater than 40 microns; and/or vi) calculating, based on the backscatter coefficients of the first and second channels, a droplet size distribution.

A further embodiment of any of the foregoing optical icing conditions detectors, wherein sampling and holding the post-peak slope of the first reflected light signal can include sampling and holding two values of the first reflected light signal by the cloud at different times subsequent to the measured time of the peak. Sampling and holding a post-peak slope of the second reflected light signal can include sampling and holding two values of the second reflected light signal at different times subsequent to the measured time of the peak. A further embodiment of any of the foregoing optical icing conditions detectors, wherein sampling and holding the post-peak slope of the first reflected light signals can include measuring a time derivative of the first reflected light signal by the cloud and determining a peak of the measured time derivative of the first reflected light signal. Sampling and holding a post-peak slope of the second reflected light signal can include measuring a time derivative of the second reflected light signal by the cloud and determining a peak of the measured time derivative of the second reflected light signal.

While the invention has been described with reference to an exemplary embodiment(s), it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. An optical icing conditions detector comprising:
   a pulsed laser system configured to generate a first pulse of circularly polarized light having a first wavelength; and
   two analog channels, each of which includes:
      a peak detector configured to generate an analog signal indicative of a peak of a light signal reflected by a cloud;
      a post-peak slope detector configured to generate, based on one or two post-peak samples of the signal reflected by the cloud, an analog signal indicative of a rate of decay of the light signal reflected by the cloud, the rate of decay corresponding to a time following a time of the detected peak; and
      a reflection fluctuation detector configured to generate an analog signal indicative of a magnitude of high-frequency fluctuation of the light signal reflected by the cloud;
   wherein a first of the two analog channels is configured to operate on a first reflected light signal corresponding to light of the first pulse reflected by the cloud, the first reflected light signal having a left-hand circular polarization;
   wherein a second of the two analog channels is configured to operate on a reflected light signal corresponding to light of the first pulse reflected by the cloud, the second reflected light signal having a right-hand circular polarization; and
   wherein a microprocessor is configured to calculate metrics, which include:
      based on the analog signal indicative of the peak and the analog signal indicative of the rate of decay, a backscatter coefficient; and/or
      based on a ratio of calculations based on analog signals from the first channel to calculations based on analog signals from the second channel, an ice/liquid ratio; and/or
      based on the magnitude of high-frequency fluctuation indicated by the analog signal generated by the reflection fluctuation detector, a measure of a density of large particles in the cloud.

2. The optical icing conditions detector of claim 1, wherein the microprocessor is configured to calculate, based on the analog signal indicative of the rate of decay, an optical extinction coefficient.

3. The optical icing conditions detector of claim 1, wherein the microprocessor is configured to calculate, based on the analog signal indicative of the peak and the signal indicative of the rate of decay, the backscatter coefficient.

4. The optical icing conditions detector of claim 1, wherein the microprocessor is configured to calculate, based on a ratio of calculations based on the analog signals from the first channel to calculations based on the analog signals from the second channel, the ice/liquid ratio.

5. The optical icing conditions detector of claim 1, wherein the microprocessor is configured to calculate, based on the magnitude of high-frequency fluctuation indicated by the analog signal generated by the reflection fluctuation detector, the measure of density of large particles in the cloud.

6. The optical icing conditions detector of claim 1, wherein the first wavelength corresponding to light having a water absorption coefficient less than 50 $m^{-1}$.

7. The optical icing conditions detector of claim 1, wherein the post-peak slope detector include two sample and hold circuits each configured to sample and hold a value of the light signal reflected by the cloud at different times.

8. The optical icing conditions detector of claim 1, wherein the post-peak slope detector includes:
   a differentiator configured to generate a signal indicative of a time derivative of the light signal reflected by the cloud; and
   a peak detector configured to generate a signal indicative of a peak of the signal indicative of the time derivative of the light signal reflected by the cloud.

9. The optical icing conditions detector of claim 1, further comprising a third analog channel which includes:
   a peak detector configured to generate an analog signal indicative of a peak of a light signal reflected by a cloud; and
   a post-peak slope detector configured to generate an analog signal indicative of a rate of decay of the light signal reflected by the cloud, the rate of decay following the time of the peak.

10. The optical icing conditions detector of claim 9, wherein the pulsed laser system is further configured to generate and a second pulse of light having a second wavelength, and wherein the third analog channel is configured to operate on a third reflected light signal corresponding to light of the second pulse reflected by the cloud.

11. The optical icing conditions detector of claim 10, wherein the second wavelength is 1550 nm corresponding to light having a water absorption coefficient greater than 1000 $m^{-1}$.

12. A method of determining icing conditions, including an ice/liquid ratio, in a cloud, the method comprising:

directing a first pulse of circularly polarized light having a first wavelength at a cloud;

sampling and holding an analog peak sample and one or two analog post-peak samples of a first reflected light signal corresponding to light of the first pulse reflected by the cloud, the first reflected light signal having a left-hand circular polarization;

sampling and holding an analog peak sample and one or two analog post-peak samples of a second reflected light signal corresponding to light of the first pulse reflected by the cloud, the second reflected light signal having a right-hand circular polarization;

determining, for at least one of the first and second reflected light signals, based on the analog peak sample and the analog post-peak samples of the signal reflected by the cloud, an extinction coefficient;

determining, for each of the first and second reflected light signals, based on the analog peak sample and the analog post-peak samples of the signal reflected by the cloud, a backscatter coefficient;

determining, based on the backscatter coefficient and the optical extinction coefficient, the ice/liquid ratio;

determining, for at least one of the first and second reflected light signals, based on an analog signal indicative of magnitude of high-frequency fluctuation, the magnitude of high-frequency fluctuation;

directing a second pulse of light having a second wavelength at the cloud;

sampling and holding an analog peak sample and one or two analog post-peak samples of a third reflected light signal corresponding to light of the second pulse reflected by the cloud;

determining, for the third reflected light signal, based on the analog peak sample and the analog post-peak samples of the third reflected light signal, a backscatter coefficient; and calculating, based on the backscatter coefficients of the first, second, and third reflected light signals, a droplet size distribution.

13. The method of claim 12, further comprising:
calculating, based on the extinction coefficient, a density of particles.

14. The method of claim 12, further comprising:
calculating, based on the measured magnitude of high-frequency fluctuation, a density of large particles in a sparse cloud, wherein large particles have an average diameter greater than 40 microns.

15. The method of claim 12, wherein sampling and holding the one or two analog post-peak samples of the first reflected light signal comprises:
sampling and holding two values of the first reflected light signal by the cloud at different times subsequent to the measured time of the peak,
wherein sampling and holding the one or two analog post-peak samples of the second reflected light signal comprises sampling and holding two values of the second reflected light signal at different times subsequent to the measured time of the peak.

16. The method of claim 12, wherein sampling and holding the one or two analog post-peak samples of the first reflected light signals comprises:
measuring a time derivative of the first reflected light signal by the cloud and determining a peak of the measured time derivative of the first reflected light signal,
wherein sampling and holding the one or two analog post-peak samples of the second reflected light signal comprises measuring a time derivative of the second reflected light signal by the cloud and determining a peak of the measured time derivative of the second reflected light signal.

* * * * *